(12) United States Patent
Carson

(10) Patent No.: US 6,746,683 B2
(45) Date of Patent: Jun. 8, 2004

(54) NONTOXIC PESTICIDE, AND METHOD OF USING THE SAME

(76) Inventor: Jack Carson, 4093 Diamond Ruby, Suite 7, Christiansted (VG)

( * ) Notice: Subject to any disclaimer, the term of this patent is extended or adjusted under 35 U.S.C. 154(b) by 0 days.

(21) Appl. No.: 10/289,351

(22) Filed: Nov. 7, 2002

(65) Prior Publication Data

US 2003/0086956 A1 May 8, 2003

Related U.S. Application Data

(60) Provisional application No. 60/331,119, filed on Nov. 8, 2001.

(51) Int. Cl.[7] ........................... A01N 25/00; A61K 9/14; A61K 47/30
(52) U.S. Cl. ..................... 424/405; 424/487; 514/772.3
(58) Field of Search ............................. 514/762, 772.3; 424/405, 487, 70.16

(56) References Cited

U.S. PATENT DOCUMENTS 4,985,251 A * 1/1991 Levy ........................... 424/404

OTHER PUBLICATIONS

Material Safety Data Sheet "30C01 Clear Seal", H–I–S Paint Manufacturing Company Inc for Sealant, Inc., May 13, 2001, pp. 1–3.
Tamms Industry Technical Data Sheet "Clearseal 300", Sep. 2000, pp 1–2.

* cited by examiner

*Primary Examiner*—Alton N Pryor
(74) *Attorney, Agent, or Firm*—Rader, Fishman & Grauer PLLC

(57) ABSTRACT

A pesticide includes a solution of a polymer that is capable of coating an exterior portion of an insect. A method of combating insect infestation includes the step of exposing an area infested with an insect with such a pesticide.

8 Claims, No Drawings

NONTOXIC PESTICIDE, AND METHOD OF USING THE SAME

The appl'n claims the benefit of Provisional Appl'n No. 60/331,119 filed Nov. 8, 2001.

FIELD OF THE INVENTION

The present invention relates to a pesticide. More particularly, the present invention relates to a nontoxic composition that kills outdoor pests such as ants without compromising the safety of the soil and the surroundings of the area where the composition is applied.

BACKGROUND OF THE INVENTION

Individual households spend hundreds of dollars every year battling infestation from flying and crawling insects. Likewise, schools, businesses, and other outdoor and indoor venues where the public work and gather must utilize time and money resources in removing insects and other pests in order to make these venues both safe and aesthetically pleasing.

Pesticides that have been determined to be effective, however, tend to be extremely poisonous and dangerous. The compositions not only kill or harm insects, but also have the potential to seriously harm humans, pets, birds, fish and other animals that come in contact with the chemicals. Consequently, the most effective, and thus toxic, formulations can not be applied to battle insect infestation in day care centers, schools, colleges, parks, commercial properties, and so forth. The government has taken notice of the harmful effects of the poisons in pesticides, and has seriously restricted or banned from sale or use the poisonous compositions.

SUMMARY OF THE INVENTION

From the above discussion, it is clear that there is a need in the art for a pesticide that includes compounds that are nontoxic to humans, pets, birds, other non-targeted organisms, at least at the concentration and amounts in which they are applied against insects such as ants. There is clearly a need for a pesticide that can be used without harmful side effects on the soil, ground water, or air in the environment where the pesticide is applied.

It is an object of the present invention to meet the above-described needs and others. Specifically, it is an object of the present invention to provide a pesticide, which includes an aqueous solution where a majority of the solution by weight is water, and a minority of the solution by weight is a water soluble polymer that adheres to an exterior portion of an insect.

It is a further object of the present invention to provide a method of combating insect infestation, which includes the steps of contacting an insect with an aqueous solution where the majority of the solution by weight is water, and a minority of the solution by weight is a water soluble polymer that adheres to an exterior portion of the insect.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve these stated and other objects, the present invention may be embodied and described as set forth in the claims.

DETAILED DESCRIPTION OF THE PREFERRED EMBODIMENTS

Although the following explanation refers to the insects as ants, clearly the principles of the invention can be applied to similar insects and pests, particularly ones that inhabit the soil. The present invention is an aqueous composition that includes one or more polymer compounds dissolved therein. The water in the solution acts as a delivery agent, which allows the composition as a whole to penetrate the soil in which the ants are bedding. Because water first tends to flow through strata of minimal density before occupying other layers of dirt, the solution follows the tunnels and loose dirt created by the ants. The aqueous solution does not migrate to the adjacent soil until the ant bed is saturated.

The polymer compounds are present at a nontoxic level, and work against insects such as ants when they come into contact with the insects due to a plurality of effects. First, once the aqueous solution contacts the ants, the polymer compounds that are in the solution contact the cilia on the ant bodies. The polymer adheres to the cilia, and as a result, the ants lose their orientation, as the cilia are the ants' main sensing organs. Second, on the ants' bodies are tiny holes through which the ants obtain oxygen necessary for respiration. The polymer compounds cover these tiny holes by adhering to the ants, and the ants suffocate. As mentioned above, many insects other than ants bear similar physical features, and consequently would be similarly affected by contact from the aqueous polymeric composition of the present invention.

The figures filed herewith exhibit dead ants after being contacted with the composition of the present invention, with the polymer from the solution adhered to the cilia, and otherwise encapsulating at least a portion of the ants, thereby suffocating them.

The composition of the present invention is an aqueous solution where at least one polymer is dissolved therein. The majority of the solution is water. Naturally, the polymer is one that is soluble in water when the polymer constitutes a minority of the solution by weight, and yet adheres to the cilia and/or the body of an ant. In a preferred embodiment of the invention, the polymer constitutes less than about 10% of the solution by weight. More preferably, the polymer constitutes between about 8% of the solution by weight, and 5% of the solution by weight. Most preferably, the polymer constitutes about 6% of the solution by weight.

The polymer is preferably one having an acrylic compound as a monomer unit, such as an acrylic acid, acrylonitryl, or some acrylate group. In a preferred embodiment of the invention, an acryl-type polymeric mixture is diluted so that the polymer is present at approximately 5.9% by weight in water. In a most preferred embodiment of the invention, an aqueous, acryl-type polymeric formulation, sold under the trade name ClearSeal™ and manufactured by Sealant, Inc. of Carson City, Nev. is diluted with water to approximately a 3:1 water:ClearSeal concentration. After mixing, the solution is ready for use.

The pesticide solution as formulated above can be applied to an infested region by pouring into an ant bed, for example. However, the solution may also be poured or sprayed directly on the ants. The solution is impervious to water and moisture penetration once the solution adheres to the ants and dries. Thus, the pesticide solution seals the ants with an impervious coating, and infiltrates the entire ant bed prior to migrating to a more dense adjacent strata.

The following is an example of the effectiveness of the solution of the present invention, relative to other pesticides presently on the market. An approximately two-acre lot of land was isolated from interference by roping off the testing area. The lot had approximately fifty-four ant beds naturally formed over an unknown amount of time. Each of the ant beds varied in size. Some measured as small as four inches in diameter, while others measured as large as twenty inches in diameter. Each ant bed was identified by a numbered flag and located on a site map. Of the fifty-four ant beds, forty-eight of them were chosen for testing. Four different products were applied, with each product being used for twelve distinct ant beds. Plain water was used on twelve of the beds as a control agent. The formulation of the most preferred embodiment of the invention described above was used on twelve distinct ant beds. A formulation of a 3:1 ratio of water:Steel Seal™ manufactured by Sealant, Inc. of Carson City, Nev. was also used on twelve distinct ant beds. Finally, a commercially available Ortho™ pesticide was used on the last twelve distinct ant beds. The Ortho™ pesticide was applied to the assigned beds. The control, the water:Steel Seal™, and the formulation of the present invention were applied to each of the ant beds in a quantity of one gallon each. The volume of one gallon was chosen strictly for consistency sake. Of course, according to the size of an ant bed, more or less of the pesticide of the present invention would be applied.

The results of the above example showed that the water-:Steel Seal was statistically ineffective, and similar to the control. The formulation of the current invention was statistically more effective than the control. In fact, the formulation of the current invention proved to be at least as effective as the Ortho™ pesticide. The effectiveness of the invention is additionally advantageous in that the formulation is nontoxic, unlike the Ortho™ pesticide. Further, in addition to providing no detrimental effects to the immediate environment and soil, the formulation is not hazardous if it comes into contact with the ground water table. Because of these advantages, the present invention can be used not only on private land, but in public parks, schools, and other areas where toxic pesticides may not be legally applied to the ground to combat ants and other insect pests.

It will be appreciated that the present invention is not limited to any of the exact constructions that have been described above and illustrated in the accompanying drawings, and that various modifications and changes can be made without departing from the scope and spirit thereof. It is intended that the scope of the invention only be limited by the appended claims. The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A pesticide, which consists of:
   an aqueous solution consisting of water and a water-soluble polymer, said solution being primarily water by weight said polymer (1) comprising at least one acrylic compound forming monomer units, (2) being an acrylic polymeric mixture, (3) being present in a concentration of less than 10% by weight, (4) being the active ingredient which kills a insect by coating an exterior portion of said insect.

2. A pesticide according to claim 1, wherein said acrylic compound is selected from the group consisting of acrylic acid, acrylonitryl, and an acrylate compound.

3. A pesticide according to claim 1, wherein said polymer is present in a concentration ranging between about 5% and about 8% by weight.

4. A pesticide according to claim 1, wherein said polymer is present in a concentration of about 6% by weight.

5. A method of combating insect infestation, which comprises the steps of:
   exposing an area that is infested with at least one insect to a pesticide which consists of an aqueous solution consisting of water and a water-soluble polymer, said solution being primarily water by weight, said polymer (1) comprising at least one acrylic compound forming monomer units, (2) being an acrylic polymeric mixture, (3) being present in a concentration of less than 10% by weight, (4) being the active ingredient which kills said insect by coating an exterior portion of said insect.

6. A method according to claim 5, wherein said acrylic compound is selected from the group consisting of acrylic acid, acrylonitryl, and an acrylate compound.

7. A method according to claim 5, wherein said polymer is present in a concentration ranging between about 5% and about 8% by weight.

8. A method according to claim 5, wherein said polymer is present in a concentration of about 6% by weight.

\* \* \* \* \*